United States Patent
Elder et al.

(10) Patent No.: US 7,947,294 B2
(45) Date of Patent: May 24, 2011

(54) SHATTER RESISTANT ENCAPSULATED COLORANTS FOR NATURAL SKIN APPEARANCE

(75) Inventors: Todd Elder, Butler, NJ (US); Christina Ligia Andrianov, Monroe, NY (US); Kishor Kumar Mistry, Bradford (GB); Janine Andrea Preston, Leeds (GB); Mark Christopher Baxter, Bradford (GB)

(73) Assignee: BASF SE, Ludwigshafen (DE)

( * ) Notice: Subject to any disclaimer, the term of this patent is extended or adjusted under 35 U.S.C. 154(b) by 920 days.

(21) Appl. No.: 11/147,741

(22) Filed: Jun. 8, 2005

(65) Prior Publication Data

US 2005/0276774 A1    Dec. 15, 2005

Related U.S. Application Data

(63) Continuation-in-part of application No. 10/903,628, filed on Jul. 30, 2004, now abandoned, which is a continuation-in-part of application No. 10/868,097, filed on Jun. 15, 2004, now abandoned.

(51) Int. Cl.
*A61K 8/72* (2006.01)

(52) U.S. Cl. .................. 424/401; 424/70.1

(58) Field of Classification Search .......... None
See application file for complete search history.

(56) References Cited

U.S. PATENT DOCUMENTS

| | | | |
|---|---|---|---|
| 4,337,185 A | 6/1982 | Wessling et al. | 524/458 |
| 4,430,468 A | 2/1984 | Schumacher | 524/109 |
| 4,879,175 A | 11/1989 | Ugro, Jr. | 428/321.5 |
| 5,070,136 A | 12/1991 | Dersch et al. | 524/555 |
| 5,151,217 A | 9/1992 | Price | 252/312 |
| 5,234,711 A | 8/1993 | Kamen et al. | 427/213.34 |
| 5,320,835 A * | 6/1994 | Pahlck et al. | 424/64 |
| 5,382,433 A * | 1/1995 | Pahlck et al. | 424/401 |
| 5,624,973 A | 4/1997 | Lu et al. | 522/40 |
| 6,060,164 A | 5/2000 | Green et al. | 428/402 |
| 6,225,372 B1 | 5/2001 | Lykke et al. | 523/201 |
| 6,280,511 B1 | 8/2001 | Schaedeli et al. | 106/31.33 |
| 6,387,991 B1 | 5/2002 | Hayes | 524/52 |
| 6,486,909 B1 | 11/2002 | Pirim | 348/143 |
| 2002/0058732 A1* | 5/2002 | Mistry et al. | 523/201 |
| 2003/0018102 A1* | 1/2003 | Weston et al. | 523/201 |
| 2005/0031558 A1 | 2/2005 | Elder et al. | 424/59 |

FOREIGN PATENT DOCUMENTS

| | | |
|---|---|---|
| EP | 0531005 | 3/1993 |
| EP | 0697423 | 2/1996 |
| WO | 98/50002 | 11/1998 |
| WO | WO 02/090445 | * 11/2002 |

OTHER PUBLICATIONS

U.S. Appl. No. 11/448,512, filed Jun. 2006, Jones et al.*
U.S. Appl. No. 11/448,353, filed Jun. 2006, Rabe et al.*

* cited by examiner

*Primary Examiner* — Frederick Krass
*Assistant Examiner* — Brian Gulledge
(74) *Attorney, Agent, or Firm* — Shiela A. Loggins; Joseph Suhadolnik; Kevin Mansfield

(57) ABSTRACT

The present invention relates to personal care or cosmetic compositions that contain a shatter-resistant blend of microencapsulated colorants that can produce a natural, textured tone effect. A method for cosmetic treatment comprises application of such personal care or cosmetic compositions onto at least a part of the body.

15 Claims, No Drawings

SHATTER RESISTANT ENCAPSULATED COLORANTS FOR NATURAL SKIN APPEARANCE

This application is a continuation-in-part of application Ser. No. 10/903,628, filed Jul. 30, 2004, abandoned, which is a continuation-in-part of application Ser. No. 10/868,097, filed Jun. 15, 2004, abandoned.

FIELD OF THE INVENTION

This invention relates to compositions containing encapsulated colorants and their use in personal care applications. More particularly this invention relates to compositions containing shatter resistant encapsulated colorant and their use in personal care applications.

BACKGROUND OF THE INVENTION

There is a need to provide particles with improved shatter resistance that can be used for a variety of applications. Specifically there is a need to provide products containing entrapped or encapsulated colorants, which products retain the colorant over extended periods and exhibit improved shatter resistance when subjected to different environments. This is particularly the case when employing oil soluble and water-soluble dyes, where it is generally difficult to permanently retain the dye. In a cosmetic composition if the dye is not permanently retained, this can impair the long-term visual effect of the cosmetic.

U.S. Pat. No. 5,234,711 describes a method for encapsulation of pigment particles utilized in ink formulations and their use for cosmetic products. The cosmetic products are especially directed to eyeliner pens.

U.S. Pat. No. 5,382,433 and published PCT Application WO 98/5002 describe the use of a cosmetic stick that contains microencapsulated pigment particles. The encapsulated pigment in the '433 patent is made by coacervation polymerization. The PCT application expands on this patent by including a volatile solvent in the cosmetic composition. The volatile solvent is present to minimize the gritty feel of the microencapsulated material.

A variety of techniques are known for providing encapsulated or entrapped colorants. For example, published PCT Application WO 91/06277 describes cosmetic formulations which have activatable dormant pigments dispersed in an anhydrous base or vehicle. A ground pigment or a liquid carrier dispersion is microencapsulated to form a stable, dry, free flowing powder of micro-sized particles. The preferred process of encapsulation is by coacervation, e.g. by emulsifying a liquid dispersion in a continuous, external aqueous phase to form micro-sized droplets and a complex of colloidal material is added to the external phase in such a way to form a deposit on or around each droplet thereby forming an outer wall or shell. The microcapsules are intended to rupture and release the dormant pigment when subjected to physical forces.

U.S. Pat. No. 5,234,711 concerns methods of encapsulating pigment particles useful in manufacturing of cosmetic products. It is an objective of this reference to employ an encapsulation process to increase the wettability, dispersibility and heat resistance of the pigment particles. The encapsulation method involves redox or free radical vinyl polymerization in an aqueous medium.

Published European Patent Application 225,799 describes a microencapsulated solid non-magnetic colorant material in a liquid, gel, wax or low temperature melting solid carrier phase, which is encapsulated within a polymeric shell. Absorbed onto the shell is a silane or titanate coupling agent, which increases the oleophilicity of the surface of the solid colorant material.

Published European Patent Application 445,342 relates to a cosmetic composition comprising a pigment that has been formed by incorporating a solvate dye into a resin and admixing with a cosmetic carrier. The amount of pigment present is sufficient to provide an attractive cosmetic effect when applied to skin, nails or hair. Any cosmetically acceptable soluble dye can be used. Any resin may be used provided it can be pulverized to a fine powder. The solvate dye may be incorporated into the resin by adding it to the elasticized or molten resin, or by dissolving the dye in a solution of unpolymerized resin and a mutual solvent for the dye and the resin, then polymerizing the resin, or by contacting the dye with the resin. The dye impregnated resin powders are said to be usable in a variety of cosmetic compositions.

WO 02/090445 addresses the problem of color retention and provides polymeric particles comprising a matrix polymer and colorant distributed throughout it. The matrix polymer is formed from a blend of monomers comprising a first monomer, which is an ethylenically unsaturated ionic monomer which is a salt of a volatile counterion and a second monomer, which is an ethylenically unsaturated hydrophobic monomer which is capable of forming a homopolymer of glass transition temperature in excess of 50° C. Typical matrix polymers include copolymers that have been formed from styrene with ammonium acrylate. The polymeric particles exhibit very good retention properties and are able to retain the colorant under an in a variety of conditions. However, these particles tend to suffer the drawback that they can fracture and even shatter under certain conditions when handled harshly, and this can lead to loss of the colorant.

Copending U.S. patent application Ser. No. 10/785, 208 describes the use of a blend of microencapsulated colorants prepared as described in WO 02/090445 in cosmetic compositions. The blend produces a textured natural tone coloring when applied, or creates similar effects on or in the cosmetic product itself. However, as noted above, the microcapsules are structurally different from those employed according to the present invention and lack their shatter-resistance.

An objective of the present invention is to provide cosmetic compositions comprising polymeric particles containing entrapped or encapsulated colorants, which compositions retain the colorant over extended periods and also when subjected to different environments. This is especially important when the colorants are oil-soluble and particularly water-soluble dyes, where it is generally difficult to permanently retain the dye. In a cosmetic composition, if the dye is not permanently retained, this can impair the visual effect of the cosmetic after prolonged use.

Encapsulation or entrapment of colorants can result in visual impairment of the colorant. This may be as a result of the polymer absorbing light from certain wavelengths or sometimes as a result of the irregular morphology of the polymer particles. This is also true where the particles are not shatter resistant. Fractures in the particles or broken particles will also lead to visual impairment of the colorant.

Thus another objective of the present invention is to provide cosmetic compositions comprising polymer-entrapped colorants in which the particles are shatter resistant and can withstand harsh handling, thus providing improved visual effects.

SUMMARY OF THE INVENTION

In one aspect the present invention provides microparticles containing an effective coloring amount of at least 1 colorant, wherein said colorant is entrapped in a matrix polymer that has been formed from a blend of monomers comprising a first monomer which is an ethylenically unsaturated ionic monomer and a second monomer which is an ethylenically unsaturated hydrophobic monomer which is capable of forming a homopolymer of glass transition temperature in excess of 50° C., wherein secondary particles are distributed throughout the matrix, which secondary particles comprise a hydrophobic polymer that has been formed from an ethylenically unsaturated hydrophobic monomer which is capable of forming a homopolymer having a glass transition temperature in excess of 50° C. and optionally other monomers, which hydrophobic polymer is different from that of the matrix polymer. The individual colorant microparticles have a typical particle size of between 1 and 60 microns.

In another aspect the present invention provides a solid or liquid personal care or cosmetic composition that comprises an effective coloring amount of a blend of at least 2 colorants, wherein said colorants are entrapped in one or more microparticulate matrix polymers that have been formed from a blend of monomers comprising a first monomer which is an ethylenically unsaturated ionic monomer and a second monomer which is an ethylenically unsaturated hydrophobic monomer which is capable of forming a homopolymer of glass transition temperature in excess of 50° C., wherein secondary particles are distributed throughout the matrix, which secondary particles comprise a hydrophobic polymer that has been formed from an ethylenically unsaturated hydrophobic monomer which is capable of forming a homopolymer having a glass transition temperature in excess of 50° C. and optionally other monomers, which hydrophobic polymer is different from that of the matrix polymer.

The colorants in the composition are selected from at least two colors that are distinct from each other. In one embodiment a blend of at least two of the primary colors yellow, red and blue is employed.

The present invention also provides a method of coloring the body that comprises application of a liquid or solid personal care or cosmetic formulation having an effective coloring amount of a blend of at least 2 microparticulate colorants as described above to at least a part of said body.

The microparticulate colorant blends according to the invention have enhanced visual performance, such as a more natural skin like appearance. Furthermore the matrix polymer does not shatter under rigorous formulation conditions or handling, thus retaining the desirable aesthetic effects during storage and use.

DETAILED DESCRIPTION OF THE INVENTION

Microparticulate particles comprising a matrix polymer and secondary particles distributed throughout the matrix, wherein the matrix polymer has been formed from a blend of monomers comprising a first monomer which is an ethylenically unsaturated ionic monomer and a second monomer which is an ethylenically unsaturated hydrophobic monomer which is capable of forming a homopolymer of glass transition temperature in excess of 50° C., in which the secondary particles comprise a hydrophobic polymer that has been formed from an ethylenically unsaturated hydrophobic monomer which is capable of forming a homopolymer of glass transition temperature in excess of 50° C. and optionally other monomers, which hydrophobic polymer is different from the matrix polymer, may be obtained by a process which comprises the steps, A) providing an aqueous phase of a polymeric salt formed from a monomer blend which comprises the first and second monomers,
B) forming the secondary particles in the aqueous phase or combining the secondary particles with the aqueous phase,
C) forming a dispersion comprising the aqueous phase in a water immiscible liquid phase, which preferably comprises an amphipathic polymeric stabilizer to form an emulsion, and
D) subjecting the dispersion to dehydration wherein water is evaporated from the aqueous particles thereby forming solid particles comprising the secondary particles distributed throughout the matrix polymer.

Preferably the first monomer used to form the matrix polymer is a salt of a volatile counterion component. During the dehydration step (D) the volatile counterion component of the salt is desirably evaporated. By this is meant that at least a part of the counterion component is evaporated. For instance, where the polymeric matrix is the ammonium salt, the volatile component ammonia will be evaporated. Consequently, during the distillation stage the matrix polymer would be converted to its free acid or free base form.

The particles useful in the invention comprise a colorant. The colorant may be selected from pigments, dyes or lakes. In the process of preparing the particles it is particularly desirable for the colorant to be dissolved or dispersed in the aqueous phase so that it can become distributed throughout the matrix polymer.

It has been found that the polymeric microparticles described above exhibit improved shatter resistance in combination with improved visual performance. Furthermore the polymer matrix does not allow the entrapped colorant to be released even under prolonged use. It is particularly desirable to provide particles in which the colorant is distributed throughout the matrix polymer and wherein the matrix polymer is impermeable to the colorant.

The polymeric products can be further enhanced if the matrix polymer is cross-linked. This cross-linking can be as a result of including a cross-linking step in the process. This can be achieved by including self cross-linking groups in the polymer, for instance monomer repeating units carrying a methylol functionality. Preferably though the cross-linking is achieved by including a cross-linking agent with the aqueous phase polymer. The cross-linking agents are generally compounds which react with functional groups on the polymer chain. For instance, when the polymer chain contains anionic groups, suitable cross-linking agents include aziridines, diepoxides, carbodiamides, silanes or multivalent metals, for instance aluminum, zinc or zirconium. A particularly preferred cross-linking agent is ammonium zirconium carbonate or zinc oxide. Another particularly preferred class of cross-linking agents includes compounds that form covalent bonds between polymer chains, for instance silanes or diepoxides.

The cross-linking process desirably occurs during the dehydration step. Thus where a cross-linking agent is included, it will generally remain dormant until the dehydration is started.

It has been found that polymers formed from the special combination of a hydrophobic monomer that is capable of forming a homopolymer of glass transition temperature in excess of 50° C., preferably greater than 60 or 80° C., exhibit considerably improved performance in regard to the impermeability to the colorant as well as other actives. By hydrophobic monomer is meant that the monomer has a solubility in water of less than 5 g per 100 ml of water.

The glass transition temperature (Tg) for a polymer is defined in the Encyclopedia of Chemical Technology, Volume 19, fourth edition, page 891, as the temperature below which (1) the transitional motion of entire molecules and (2) the coiling and uncoiling of 40 to 50 carbon atom segments of chains are both frozen. Thus, below its Tg a polymer would not exhibit flow or rubber elasticity.

The Tg of a polymer may be determined using Differential Scanning Calorimetry (DSC).

Generally the average particle size diameter of the particles is less than about 100 microns. Preferably the average particle size diameter is in the range of about 1 to 60 microns, e.g. 1 to 40 microns and especially between 1 and 30 microns. Average particle size is determined by a Coulter particle size analyzer according to standard procedures well documented in the literature.

Without being limited to theory it is believed that the particular combination of an ionic monomer and a hydrophobic monomer provides polymers with the right degree of hydrophilicity and hardness that seems to be responsible for the improvements in impermeability to the colorant as well as other actives. The presence of the secondary particles comprising a hydrophobic polymer appears to be responsible for providing the particles with improved shatter resistance.

Typically the monomer blend in for making the matrix polymer may contain at least 50% by weight hydrophobic monomer, the remainder being made up of ionic monomer. Generally though the hydrophobic monomer will be present in amounts of at least 60% by weight.

Preferred compositions contain between 65 and 90% by weight hydrophobic polymer, for instance around 70 or 75%.

Specific examples of hydrophobic monomers include styrene, methyl methacrylate, tertiary butyl methacrylate, phenyl methacrylate, cyclohexyl methacrylate and isobornyl methacrylate.

It has been found that it is not possible to replace the hydrophobic monomers with ethylenically unsaturated carboxylic acid esters that are not capable of forming a homopolymer that has a glass transition temperature of at least 50° C. without adversely increasing the permeability of the polymer. Preferably still the Tg should be at least 60° C. or even at least 80° C. For instance, substituting the hydrophobic monomers employed in the present invention by other (meth) acrylic esters, for instance 2-ethyl hexyl acrylate would be unsuitable. The best results are generally obtained by use of monomers which are capable of forming polymers of very high Tg. Therefore less preferred products would be produced using ethyl acrylate or propyl acrylate as the hydrophobic monomer.

The ionic monomer may contain either anionic or cationic groups, or alternatively may be potentially ionic, for instance in the form of an acid anhydride. Preferably the ionic monomer is an ethylenically unsaturated anionic or potentially anionic monomer. Suitable anionic or potentially anionic monomers include acrylic acid, methacrylic acid, ethacrylic acid, fumaric acid, maleic acid, maleic anhydride, itaconic acid, itaconic acid anhydride, crotonic acid, vinyl acetic acid, (meth) allyl sulfonic acid, vinyl sulfonic acid and 2-acrylamido-2-methyl propane sulfonic acid. Preferred anionic monomers are carboxylic acids or acid anhydrides.

When the ionic monomer is anionic, for instance a carboxylic acid or anhydride, the volatile counterion may be ammonia or a volatile amine component. Generally the volatile amine component will be a liquid that can be evaporated at low to moderate temperatures, for instance by temperatures up to 200° C. Preferably, it will be possible to evaporate the volatile amine under reduced pressure at temperatures below 100° C. Thus the polymer may be produced in free acid form and then neutralized with an aqueous solution of ammonium hydroxide or a volatile amine, for instance ethanolamine, methanolamine, 1-propanolamine, 2-propanolamine, dimethanolamine or diethanolamine. Alternatively the polymer may be prepared by copolymerizing the ammonium or volatile amine salt of an anionic monomer with the hydrophobic monomer.

Generally, the matrix polymer may be prepared by any suitable polymerization process. For instance the polymer can be conveniently prepared by aqueous emulsion polymerization for instance as described in EP-A-697423 or U.S. Pat. No. 5,070,136. The polymer can then be neutralized by the addition of an aqueous solution of ammonium hydroxide or a volatile amine.

In a typical polymerization process, the blend of hydrophobic monomer and anionic monomer is emulsified into an aqueous phase which contains a suitable amount of emulsifying agent. Typically, the emulsifying agent may be any commercially available emulsifying agent suitable for forming aqueous emulsion. Desirably these emulsifying agents will tend to be more soluble in the aqueous phase than in the water immiscible monomer phase and thus will tend to exhibit a high hydrophilic lipophilic balance (HLB). Emulsification of the monomer may be effected by known emulsification techniques, including subjecting the monomer/aqueous phase to vigorous stirring or shearing or alternatively passing the monomer/aqueous phase through a screen or mesh. Polymerization may then be effected by use of a suitable initiator system, for instance a UV initiator or thermal initiator. A suitable technique of initiating the polymerization would be to elevate the temperature of an aqueous emulsion of monomer to above 70 or 80° C. and then add between 50 and 1000 ppm of ammonium persulfate by weight of monomer.

Generally the matrix polymer has a molecular weight of up to 200,000 (determined by GPC using standard industrial parameters). Preferably the polymer has a molecular weight of below 50,000, for instance 2,000 to 20,000. Usually the optimum molecular weight for the matrix polymer is around 6,000 to 12,000.

A particularly preferred matrix polymer is a copolymer of styrene with ammonium acrylate. More preferably this polymer is used when the process employs a cross-linking agent, which is especially ammonium zirconium carbonate or zinc oxide.

In an alternative version of the process, the ionic monomer may be cationic or potentially cationic, for instance an ethylenically unsaturated amine. In this form of the invention the volatile counterionic component is a volatile acid component. Thus, in this form of the invention the matrix polymer can be formed in an analogous way to the aforementioned anionic matrix polymer, except that the anionic monomer is replaced by a cationic or potentially cationic monomer. Generally where the polymer is prepared in the form of a copolymer of a free amine and hydrophobic monomer, it is neutralized by including a suitable volatile acid, for instance acetic acid, formic acid, propanoic acid, butanoic acid or even carbonic acid. Preferably the polymer is neutralized by a volatile carboxylic acid.

Suitable cationic or potentially cationic monomers include dialkyl aminoalkyl (meth) acrylates, dialkyl aminoalkyl (meth) acrylamides or allyl amines and other ethylenically unsaturated amines and their acid addition salts. Typically the dialkyl aminoalkyl (meth) acrylates include dimethyl aminomethyl acrylate, dimethyl aminomethyl methacrylate, dimethyl aminoethyl acrylate, dimethyl aminoethyl methacrylate, diethyl aminoethyl acrylate, diethyl aminoethyl methacrylate, dimethyl aminopropyl acrylate, dimethyl aminopropyl methacrylate, diethyl aminopropyl acrylate, diethyl aminopropyl methacrylate, dimethyl aminobutyl acrylate, dimethyl aminobutyl methacrylate, diethyl aminobutyl acrylate and diethyl aminobutyl methacrylate. Typically the dialkyl aminoalkyl (meth) acrylamides include dimethyl aminomethyl acrylamide, dimethyl aminomethyl methacrylamide, dimethyl aminoethyl acrylamide, dimethyl aminoethyl methacrylamide, diethyl aminoethyl acrylamide, diethyl aminoethyl methacrylamide, dimethyl aminopropyl acrylamide, dimethyl aminopropyl methacrylamide, diethyl aminopropyl acrylamide, diethyl aminopropyl methacrylamide, dimethyl aminobutyl acrylamide, dimethyl aminobutyl methacrylate, diethyl aminobutyl acrylate and diethyl aminobutyl methacrylamide. Typically the allyl amines include diallyl amine and triallyl amine.

The secondary particles comprise a hydrophobic polymer that has been formed from an ethylenically unsaturated hydrophobic monomer which is capable of forming a homopolymer of glass transition temperature in excess of 50° C. and optionally other monomers, which hydrophobic polymer is different from the matrix polymer. The ethylenically unsaturated hydrophobic monomer may be any of the monomers defined above in respect of the second monomer used to form the matrix polymer. Preferably, the hydrophobic monomer is the same as the second monomer used to form the matrix polymer. Specific examples of said hydrophobic monomers include styrene, methyl methacrylate, tertiary butyl methacrylate, phenyl methacrylate, cyclohexyl methacrylate and isobornyl methacrylate. Preferably the hydrophobic monomer is styrene.

The hydrophobic monomer may be polymerized alone or alternatively may optionally be polymerized with one or more other hydrophobic monomers as defined above. It may be possible to include other monomers that are not hydrophobic monomers capable of forming a homopolymer of glass transition temperature in excess of 50° C., provided that such monomers do not bring about any deleterious effects. The other monomer may be a hydrophobic monomer, for instance longer chain alkyl and esters of acrylic or methacrylic acid, such as 2-ethylhexyl acrylate or stearyl acrylate. Typically, where such monomers are included, they should be present in an amount of no more than 20% by weight based on to weight of monomers used for the secondary particles. Preferably, these monomers will be present in amount less than 10% by weight and more preferably less than 5% by weight.

Alternatively the other monomer may be a hydrophilic monomer. The hydrophilic monomer may be nonionic, for instance acrylamide, or it can be ionic, for instance as defined in respect of the first monomer used to form the matrix polymer. Generally, such monomers tend to be used in smaller proportions so that the polymer is hydrophobic. Where such monomers are included, they should be present in an amount of no more than 20% by weight based on to weight of monomers used for the secondary particles. Preferably, these monomers will be present in an amount less than 10% by weight and more preferably less than 5% by weight.

It is particularly preferred that the secondary particles comprise a hydrophobic polymer that has been formed entirely from one or more ethylenically unsaturated hydrophobic monomer(s) which is/are capable of forming a homopolymer of glass transition temperature in excess of 50° C. A particularly suitable hydrophobic polymer is a copolymer of styrene and methyl methacrylate or a homopolymer of styrene. The polymer of styrene with methyl methacrylate generally will comprise at least 40% by weight styrene and up to 60% by weight methyl methacrylate. Preferably, the copolymer will have a weight ratio of styrene to methyl methacrylate of between 50:50 to 95:5 and more preferably 60:40 to 80:20, particularly preferably 70:30 to 75:25.

Generally, the secondary particles will have an average particle size of below 1 micron, and usually below 750 nm. Preferably, the secondary particles will have an average particle size in the range between 50 and 500 nm. The secondary particles may be prepared by any conventional means. Typically, the particles may be prepared by aqueous emulsion polymerization. Preferably, the particles are prepared by aqueous microemulsion polymerization according to any typical microemulsion polymerization process documented in the prior art, for instance as described in EP-A-531005 or EP-A449450.

Typically, the secondary particles may be prepared by forming a microemulsion comprising a continuous aqueous phase (between 20 and 80% by weight), a dispersed oil phase comprising the monomer (between 10 and 30% by weight), and surfactant and/or stabilizer (between 10 and 70% by weight). Generally the surfactant and/or stabilizer will exist predominantly in the aqueous phase. A preferred surfactant and/or stabilizer is an aqueous solution of the polymer used to form the polymeric matrix. A particularly preferred surfactant/stabilizer is a copolymer of ammonium acrylate with styrene, as defined above in relation to the matrix polymer.

Polymerization of the monomer in the microemulsion can be effected by a suitable initiation system, for instance a UV initiator or thermal initiator. A suitable technique of initiating the polymerization is, for instance, to elevate the temperature of the aqueous emulsion of monomer to above 70 or 80° C. and then to add between 50 and 1000 ppm of ammonium persulfate or an azo compound such as azodiisobutyronitrile by weight of monomer. Alternatively, a suitable peroxide, e.g. a room-temperature curing peroxide, or a photo-initiator may be used. It may be preferred that polymerization is carried out at about room temperature, e.g. with a photoinitiator.

Generally the secondary particles comprise a polymer that has a molecular weight of up to 2,000,000 (determined by GPC using the standard industrial parameters). Preferably the polymer has a molecular weight of below 500,000, for instance 5,000 to 300,000. Usually the optimum molecular weight for the polymeric secondary particles is between 100,000 and 200,000.

It is preferred that the secondary particles have a core shell configuration in which the core comprises the hydrophobic polymer surrounded by a polymeric shell. More preferably the secondary particles comprise a core comprising the hydrophobic polymer and a shell comprising the matrix polymer. It is particularly preferable that the shell of matrix polymer is formed around the core of hydrophobic polymer and during polymerization.

As indicated previously the particles of the invention comprise a colorant. They may additionally comprise further active ingredients, for instance UV absorbers, UV reflectors, flame retardants or active dye tracer materials.

The particles entrap one or more colorants, and the colorant may be any colorant, for instance a dye, pigment or lake. Typical suitable colorants include any organic or inorganic pigment or colorant approved for use in cosmetics by CTFA and the FDA such as lakes, iron oxides, titanium dioxide, iron sulfides or other conventional pigments used in cosmetic formulations.

Examples of pigments include inorganic pigments such as carbon black, D&C Red 7, calcium lake, D&C Red 30, talc lake, D&C Red 6, barium lake, russet iron oxide, yellow iron oxide, brown iron oxide, talc, kaolin, mica, mica titanium, red iron oxide, magnesium silicate and titanium oxide; and organic pigments such as Red No. 202, Red No. 204, Red No. 205, Red No. 206, Red No. 219, Red No. 228, Red No. 404, Yellow No. 205, Yellow No. 401, Orange No. 401 and Blue No. 404. Examples of vat dyes are Red No. 226, Blue No. 204 and Blue No. 201. Examples of lake dyes include various acid dyes which are laked with aluminum, calcium or barium.

In one embodiment the colorant is an aqueous solution of a water-soluble dye. Such dyes may include FD&C Blue No. 11, FD&C Blue No. 12, FD&C Green No. 13, FD&C Red No. 13, FD&C Red No. 140, FD&C Yellow No. 15, FD&C Yellow No. 16, D&C Blue No. 14, D&C Blue No. 19; D&C Green No. 15, D&C Green No. 16, D&C Green No. 18, D&C Orange No. 14, D&C Orange No. 15, D&C Orange No. 110, D&C Orange No. 111, D&C Orange No. 117, FD&C Red No. 14, D&C Red No. 16, D&C Red No. 17, D&C Red No. 18, D&C Red No. 19, D&C Red No. 117, D&C Red No. 119, D&C Red No. 121, D&C Red No. 122, D&C Red No. 127, D&C Red No. 128, D&C Red No. 130, D&C Red No. 131, D&C Red No. 134, D&C Red No. 139, FD&C Red No. 140, D&C Violet No. 12, D&C Yellow No. 17, Ext. D&C Yellow No. 17, D&C Yellow No. 18, D&C Yellow No. 111, D&C Brown No. 11, Ext. D&C Violet No. 12, D&C Blue No. 16 and D&C Yellow No. 110.

The above dyes are well known, commercially available materials, with their chemical structure being described, e.g., in 21 C.F.R. Part 74 (as revised Apr. 1, 1988) and in the CTFA Cosmetic Ingredient Handbook, (1988), published by the Cosmetics, Toiletry and Fragrances Association, Inc. These publications are incorporated herein by reference.

The certified dyes can be water-soluble or, preferably, lakes thereof. Lakes are organic pigments prepared by precipitating a soluble dye on a reactive or absorbent stratum, which is an essential part of the pigment's composition. Most lakes are aluminum, barium or calcium derived. These insoluble pigments are used mostly in makeup products, either powders or liquids, when a temporary color is desired that won't stain the skin (as oil-soluble dyes tend to do). The lakes are used in these products along with inorganic colors such as iron oxide, zinc oxide and titanium dioxide (the whitest white pigment).

The colorant can also be a substance that is a dormant colorant, for instance a color former that exhibits a color on exposure to a suitable trigger mechanism, for instance heat or irradiation. Suitably such entrapped color formers can be coated onto or incorporated into suitable substrates and then treated to exhibit the color. The advantage of providing color formers as polymeric particles is that they can be more easily be processed and incorporated into the substrate in a desired way. The color former can still be activated even though it is entrapped within the polymer particle.

The following tables list currently available dyes and colorants approved for use in food, drugs and/or cosmetics. The selected colorant for use herein is preferably selected from the following exemplary lists.

TABLE 1

Dyes certified for use in foods, drugs, cosmetics (FDC colors)

| | | |
|---|---|---|
| FD&C Blue No. 1 | FD&C Green No. 3 | FD&C Red No. 4 |
| FD&C Red No. 40 | FD&C Yellow No. 5 | FD&C Yellow No. 6 |

TABLE 2

Dyes certified for topically applied drugs and cosmetics

| | | |
|---|---|---|
| Ext. DC Violet #2 | Ext. D&C Yellow No. 7 | Ext. D&C Violet No. 2 |
| D&C Brown No. 1 | FD&C Red No. 4 | D&C Red No. 17 |
| D&C Red No. 31 | D&C Red No. 34 | D&C Red No. 39 |
| D&C Violet No. 2 | D&C Blue No. 4 | D&C Green No. 6 |
| D&C Green No. 8 | D&C Yellow No. 7 | D&C Yellow No. 8 |
| D&C Yellow No. 11 | D&C Orange No. 4 | D&C Orange No. 10 |
| D&C Orange No. 11 | | |

TABLE 3

Dyes certified for drugs and foods only

| | | |
|---|---|---|
| D&C Blue No. 4 | D&C Brown No. 1 | D&C Green No. 5 |
| D&C Green No. 6 | D&C Green No. 8 | D&C Orange No. 4 |
| D&C Orange No. 5 | D&C Orange No. 10 | D&C Orange No. 11 |
| D&C Red No. 6 | D&C Red No. 7 | D&C Red No. 17 |
| D&C Red No. 21 | D&C Red No. 22 | D&C Red No. 27 |
| D&C Red No. 28 | D&C Red No. 30 | D&C Red No. 31 |
| D&C Red No. 33 | D&C Red No. 34 | D&C Red No. 36 |
| D&C Violet No. 2 | D&C Yellow No. 7 | D&C Yellow No. 8 |
| D&C Yellow No. 10 | D&C Yellow No. 11 | |

Some color additives are exempt from certification and permanently listed for cosmetic use, including aluminum powder, annatto, bismuth oxychloride, bronze powder, caramel, carmine, beta-carotene, chromium hydroxide green, chromium oxide green copper (metallic powder), dihydroxyacetone, disodium EDTA-copper, ferric ammonium ferrocyanide, ferric ferrocyanide, guanine (pearl essence), guaiazulene (azulene), iron oxides, luminescent zinc sulfide, manganese violet, mica, pyrophyllite, silver (for coloring fingernail polish), titanium dioxide, ultramarines (blue, green, pink, red & violet), and zinc oxide.

The process to make the colored particles of the present invention involves dispersing the aqueous solution of matrix polymer containing a colorant into a water-immiscible liquid. Typically the water-immiscible liquid is an organic liquid or blend of organic liquids. The preferred organic liquid is a mixture of non-volatile paraffin oil and volatile paraffin oil. The two oils may be used in equal proportions by weight, but generally it is often preferred to use the non-volatile oil in excess, for instance greater than 50 to 75 parts by weight of the non-volatile oil to 25 to less than 50 parts by weight of the volatile oil.

In the process it is desirable to include a polymeric amphipathic stabilizer in the water-immiscible liquid. The amphipathic stabilizer may be any suitable commercially available amphipathic stabilizer, for instance HYPERMER® (available from ICI). Suitable stabilizers also include the stabilizers described in WO-A-97/24179.

Although it is possible to include other stabilizing materials in addition to the amphipathic stabilizer, such as surfactants, it is generally preferred that the sole stabilizing material is the amphipathic stabilizer.

In the process the dehydration step can be achieved by any convenient means. Desirably subjecting the dispersion in oil to vacuum distillation can effect dehydration. Generally this will require elevated temperatures, for instance temperatures of 30° C. or higher. Although it may be possible to use much higher temperatures e.g. 80 to 90° C., it is generally preferred to use temperatures of below 60 or 70° C.

Instead of vacuum distillation it may be desirable to effect dehydration by spray drying. Suitably this can be achieved by the spray drying process described in WO-A-97/34945.

The dehydration step removes water from the aqueous solution of matrix polymer and also the volatile counterion component, resulting in a dry polymer matrix, which is insoluble and non-swellable in water, containing therein the colorant, which is distributed throughout the polymeric matrix.

Encapsulated colorant microspheres having average diameters of 0.1 to 60 microns are preferred, for example 1 to 40 and especially 1 to 30 microns.

Depending on the intended use, the preferred average diameters will vary. For example one embodiment of this invention may be a liquid facial cosmetic formulation comprising at least 2 encapsulated colorants and having a preferred particle sizes of between 10 and 30 microns. Another embodiment may be a lipstick formulation comprising at least 2 encapsulated colorants having preferred particle sizes of between 1 and 10 microns.

It has been found that applying a personal care or cosmetic formulation composition comprising (micro)encapsulated colorants incorporated therein produces desirable effects upon application. Notably, the compositions containing a blend of at least 2 microencapsulated colorants having unique and distinct colors, particularly a blend of more than one primary color, are effective means for producing natural, textured skin tone effects. The primary colors are understood to mean red, yellow and blue. An additional feature of the inventive encapsulates is the elimination of milling or grinding often encountered with non-encapsulated colorants.

In one embodiment the personal care or cosmetic composition comprises a blend of microencapsulated colorants that are individually provided in at least 2 separate matrix polymer materials. In another embodiment at least 2 microencapsulated colorants are present within a single matrix polymer material.

The personal care or cosmetic composition according to the invention comprises from 0.1 to 70% by weight, for example from 1 to 50% by weight, and especially from 5 to 35% by weight based on the total weight of the composition, of at least 2 encapsulated colorants as well as a cosmetically tolerable carrier or adjuvant. While water is cosmetically tolerable, and in most instances will also be present, the phrase "a cosmetically tolerable carrier or adjuvant" is intended to refer to at least one substance other than water that is customarily employed in personal care or cosmetic compositions.

The personal care or cosmetic preparation according to the invention may be formulated as a water-in-oil or oil-in-water emulsion, as a vesicular dispersion of an ionic or non-ionic amphiphilic lipid, as a gel, or a solid stick. Preferably the cosmetic preparation is in the form of a liquid.

As a water-in-oil or oil-in-water emulsion, the personal care or cosmetic preparation preferably contains from 5 to 50% of an oily phase, from 5 to 20% of an emulsifier and from 30 to 90% water. The oily phase may contain any oil suitable for cosmetic formulations, e.g. one or more hydrocarbon oils, a wax, natural oil, silicone oil, a fatty acid ester or a fatty alcohol.

Cosmetic liquids may include minor amounts, for example up to 10 weight percent of mono- or polyols such as ethanol, isopropanol, propylene glycol, hexylene glycol, glycerol or sorbitol.

Cosmetic formulations according to the invention may be contained in a wide variety of cosmetic preparations. Especially the following preparations, for example, come into consideration:

skin-care preparations, e.g. skin emulsions, multi-emulsions or skin oils and body powders;

cosmetic personal care preparations, e.g. facial make-up in the form of lipsticks, lip gloss, eye shadow, liquid make-up, day creams or powders, facial lotions, creams and powders (loose or pressed); and light-protective preparations, such as sun tan lotions, creams and oils, sun blocks and pretanning preparations.

Depending upon the form of the personal care preparation, it will comprise, in addition to the encapsulated colorants, further constituents, for example sequestering agents, additional non-encapsulated colorants, perfumes, thickening or solidifying (consistency regulating) agents, emollients, UV absorbers, skin-protective agents, antioxidants and preservatives.

Compositions according to the invention may be prepared by physically blending suitable encapsulated colorants into personal care formulations by methods that are well known in the art. The examples illustrate several such methods.

The present invention also provides a method of coloring the body that comprises application of a liquid or solid personal care or cosmetic formulation having an effective coloring amount of a blend of at least 2 encapsulated colorants as described above to at least a part of said body.

In one embodiment of the method, the personal care or cosmetic formulation comprises from 0.1 to 70% by weight, for example from 1 to 50% by weight, and especially from 5 to 35% by weight based on the total weight of the formulation, of at least 2 microencapsulated colorants as described above.

In one embodiment of the method, the personal care or cosmetic composition comprises a blend of at least 2 microencapsulated colorants that are individually provided in separate matrix polymer materials. In another embodiment at least 2 microencapsulated colorants are present within a single matrix polymer material.

In one embodiment of the method, the personal care or cosmetic composition is formulated as a water-in-oil or oil-in-water emulsion, as an alcoholic or alcohol-containing formulation, as a vesicular dispersion of an ionic or non-ionic amphiphilic lipid, as a gel, or a solid stick.

In various embodiments of the method, the personal care or cosmetic composition is in the form of a skin-care preparation, a cosmetic personal care preparation or a light-protective preparation.

The following examples describe certain embodiments of this invention, but the invention is not limited thereto. It should be understood that numerous changes to the disclosed embodiments could be made in accordance with the disclosure herein without departing from the spirit or scope of the invention. These examples are therefore not meant to limit the scope of the invention. Rather, the scope of the invention is to be determined only by the appended claims and their equivalents. In these examples all parts given are by weight unless otherwise indicated.

Example 1

Shatter-resistant yellow colored micro-beads comprising 60% colorant and 40% crosslinked polymer by weight are prepared as follows:—

An aqueous phase is prepared by diluting 488 g of 46% polymer microemulsion containing 32% by weight of a styrene-methyl methacrylate copolymer (70/30 weight % monomer ratio, molecular weight 200,000) microemulsion and a 14 weight % of a styrene-acrylic acid copolymer (65/35 weight % monomers ratio, molecular weight 6,000) with 790 g of water and then milling 313 g of Yellow #10 Al lake powder (ex-Kingfisher) and 56 g titanium dioxide under a high speed mixer. To the resulting aqueous pigment dispersion is added 19 g of 50% aqueous solution of ammonium zirconium carbonate.

Separately, an oil phase is prepared by diluting 76 g of 20% an amphipathic stabilizer (90 weight % stearyl methacrylate, 10 weight % methacrylic acid copolymer, molecular weight 40,000) with 1800 g of Isopar G solvent (available from Exxon Mobil). The above aqueous phase is added to this oil phase under a high shear homogenizer to form a water-in-oil emulsion having a mean aqueous droplet particle diameter of 20 microns. The formed emulsion is transferred to a 1-liter reactor set up for vacuum distillation. The emulsion is warmed to 60° C. and then subjected to vacuum distillation to remove a water/Isopar G solvent mixture. Vacuum distillation is continued to 100° C. until no further water is collected in the distillate. Next, the reactor contents are held for further 1 hour to complete the crosslinking reaction between the zirconium crosslinker and the carboxylated supported resin.

After this heat treatment step, the reactor contents are cooled to 25° C. and the colored micro-beads formed are isolated by filtration and oven drying at 90° C.

The final product is free flowing yellow micro-beads having a mean particle size diameter of 20 microns.

Example 2

Red colored micro-beads were prepared in the same manner as described in Example 1 except that 313 g of Red # 7 calcium lake powder (ex-Kingfisher) was used instead of the Yellow # 10 aluminum lake powder.

Example 3

Blue colored micro-beads were prepared in the same manner as described in Example 1 except that 313 g of Blue # 1 aluminum lake powder (ex-Kingfisher) was used instead of the Yellow # 10 aluminum lake powder.

Example 4

This example illustrates the shatter resistance of the colored microbeads obtained by this invention.

30 grams of yellow micro-beads of Example 1 were added to 270 g of Isopropyl myristate. The resulting micro-bead slurry was warmed to 75° C. and then homogenized for 30 minutes at 6,000 rpm with a high shear mixer. After this treatment the mixture was cooled to room temperature and the micro-beads examined under a light microscope. The light microscope showed that the colored particles made according to this invention remained intact after this harsh treatment.

Example 5

An aqueous phase is prepared by diluting 200 g of a 46% polymer micro emulsion (a styrene-methyl methacrylate copolymer micro emulsion stabilized with a styrene-acrylic acid copolymer) with 100 g of water. Into this 31 g of Blue #1 Al lake powder (ex Kingfisher) is dispersed with a high shear mixer. To the resultant dispersion, a slurry comprising 20 g of zinc oxide hydrate in 80 g water, is added.

Separately, an oil phase is prepared by dilution 44 g of a 20% amphipathic stabilizer (comprised of a stearyl methacrylate (90 wt %)—Methacrylic acid copolymer (10 wt %)) with 600 g of Isopar G (ex Exxon Mobil).

The aqueous phase is dispersed into the oil phase with the aid of a high shear homogeniser to form a water-in-oil emulsion with a mean particle diameter of 20 microns. This emulsion is transferred into a set of apparatus equipped for distillation. The emulsion is warmed to 50° C. and subjected to vacuum distillation and heating (maximum temperature 100° C.) until no more water is collected in the distillate. After this, the reactor contents are held at about 100° C. for a further hour to complete the crosslinking reaction. Once this is complete, the reaction mass is cooled to 25° C. and filtered to recover the coloured beads. Finally the beads are oven dried at 90° C. to yield a free flowing blue powder with a mean particle diameter of 20 microns.

The following examples illustrate the use of the inventive colorants in various cosmetic or personal care formulations.

Lipstick

| Phase | INCI Name | Trade Name | Supplier | Parts |
|---|---|---|---|---|
| A | Castor Oil | Lipovol CO | Lipo | 33.25 |
| A | Triethylhexanoin | Schercemol GTO | Scher | 7.50 |
| A | Triisostearyl Trilinoleate | Schercemol TIST | Scher | 15.00 |
| A | Triisostearyl Citrate | Schercemol TISC | Scher | 17.50 |
| A | *Euphorbia Cerifera* (Candelilla) Wax | Refined Candelilla Wax Prills | Ross Waxes | 7.00 |
| A | *Copernicia Cerifera* (Carnauba) Wax | Yellow Carnuba Wax Flakes | Ross Waxes | 1.80 |
| A | Ozokerite | White Ozokerite Wax 77W | Ross Waxes | 1.80 |
| A | Microcyrstalline Wax | Microcrystalline Wax 1275W | Ross Waxes | 3.50 |
| A | Hydroxylated Lanolin | Ritahydrox | Rita | 1.00 |
| A | Methylparaben | Nipagin M | Clariant | 0.20 |
| A | Propylparaben | Nipasol M | Clariant | 0.10 |
| B | Colorant | Encapsulated Red Pigment | Ciba Specialty Chemicals | 5.70 |
| B | Colorant | Encapsulated Yellow Pigment | Ciba Specialty Chemicals | 1.10 |
| B | Colorant | Encapsulated Blue Pigment | Ciba Specialty Chemicals | 0.20 |
| B | Mica | Cosmetic BC Mica # 280 | Whittacker, Clark & Daniels | 4.35 |
| | | | Total | 100.00 |

Procedure:

Phase A is combined, heated to between 90-105° C. and mixed until uniform. Phase B is then added with stirring until homogenous. The temperature is maintained above 70° C. as the lipstick is poured into molds.

Medium Protection Sunscreen

| Phase | INCI Name | Trade name | Supplier | Parts |
|---|---|---|---|---|
| A | Deionized Water | DI Water | N/A | 84.86 |
| A | Propylene Glycol (and) Diazolidinyl Urea (and) Methylparaben (and) Propylparaben | Germaben II | ISP | 1.00 |
| A | *Aloe Barbadensis* Leaf Juice | Aloe Gel 1:1 Natural | Tri-K Industries | 1.00 |
| A | Propylene Glycol | Propylene Glycol | Dow Chemical | 2.50 |
| A | Butylene Glycol (and) Water (and) *Juglans Nigra* (Black Walnut) Shell Extract | Actiphyte of Black Walnut Hull | Active Organics | 0.04 |
| A | Ethyhexyl Salicylate | Escalol 587 | ISP | 5.00 |
| A | Ethylhexyl Methoxycinnamate | Escalol 557 | ISP | 3.00 |
| B | Sodium Acrylates Copolymer (and) Paraffinum Liquidum (and) PPG-1 Trideceth-6 | Ciba ® SALCARE ® SC91 | Ciba Specialty Chemicals | 2.00 |
| C | Colorant | Encapsulated Red Pigment | Ciba Specialty Chemicals | 0.20 |
| C | Colorant | Encapsulated Blue Pigment | Ciba Specialty Chemicals | 0.10 |
| D | Fragrance | Flowers in the mist | Belle Aire Fragrances | 0.30 |
|   |   | Total |   | 100.00 |

Procedure:

In an appropriate vessel add Part A and start moderate agitation.
Add part B and mix until uniform.
Add Part C; then part D and mix until well blended.

Talc Free Loose Face Powder

| Phase | INCI Name | Trade Name | Supplier | Parts |
|---|---|---|---|---|
| A | Mica | Sericite PHN | Presperse | 81.45 |
| A | Polymethyl Methacrylate | Ganzpearl GM-0600W | Presperse | 5.00 |
| A | Synthetic Wax and Corn Gluten Protein | Microease 110XF | Presperse | 2.00 |
| A | Titanium Dioxide | Titanium Dioxide 3228 | Whittaker, Clark & Daniels | 5.00 |
| A | Methylparaben | Nipagin M | Clariant | 0.20 |
| A | Propylparaben | Nipasol M | Clariant | 0.10 |
| A | Imidazolidinyl Urea | Germall 115 | ISP | 0.25 |
| B | Colorant | Encapsulated Red Pigment | Ciba Specialty Chemicals | 1.00 |
| B | Colorant | Encapsulated Yellow Pigment | Ciba Specialty Chemicals | 5.00 |
|   |   | Total |   | 100.00 |

Procedure:

Mill together A until fully dispersed. Add B to A and blend until uniform.

Oil-in-Water Facial Foundation

| Phase | INCI Name | Trade Name | Supplier | Parts |
|---|---|---|---|---|
| A | Deionized water | DI Water | N/A | 53.94 |
| A | 10% KOH solution | 10% KOH solution | N/A | 1.30 |
| A | PEG-12 Dimethicone | DC 193 Surfactant | Dow Corning | 0.10 |
| A | Talc | Talc | Whittaker, Clark & Daniels | 0.72 |
| B | 1,3-Butylene Glycol | Jeechem BUGL | Jeen Int. | 4.00 |
| B | Magnesium Aluminum Silicate | Veegum Granules | R. T. Vanderbilt | 1.00 |
| C | 1,3-Butylene Glycol | Jeechem BUGL | Jeen Int. | 2.00 |
| C | Cellulose Gum | CMC 7MF | Hercules | 0.12 |
| C | Methylparaben | Nipagin M | Clariant | 0.02 |
| D | Di-PPG-3 Myristyl Ether Adipate | Cromollient DP3-A | Croda | 14.00 |
| D | Diethyl Hexyl Maleate | Pelemol DOM | Phoenix | 4.00 |
| D | Steareth-10 | Lipocol S-10 | Lipo | 2.00 |
| D | Steareth-2 | Lipocol S-2 | Lipo | 0.50 |
| D | Cetyl Alcohol | Crodacol C-95 NF | Croda | 0.62 |
| D | Dicetyl Phosphate and Ceteth-10 Phosphate and Ceteryl Alcohol | Crodafos CES | Croda | 4.00 |
| D | Propyl Paraben | Nipasol M | Clariant | 0.10 |
| E | Colorant | Encapsulated $TiO_2$ | Ciba Specialty Chemicals | 7.50 |
| E | Colorant | Encapsulated Yellow Pigment | Ciba Specialty Chemicals | 2.50 |

| Phase | INCI Name | Trade Name | Supplier | Parts |
|---|---|---|---|---|
| E | Colorant | Encapsulated Red Pigment | Ciba Specialty Chemicals | 1.20 |
| E | Colorant | Encapsulated Blue Pigment | Ciba Specialty Chemicals | 0.20 |
| F | DMDM Hydantoin | Mackstat DM | McIntyre Group | 0.18 |
|   |   |   | Total | 100.00 |

Procedure:

Combine ingredients in phase A using a homogenizer and begin heating to 80° C. Add phase B and C and homogenize for 1 hour. In a separate beaker combine ingredients in phase D, heat to 80° C. and mix until uniform. After all ingredients in phase D have become uniform slowly add to the main phase while continuing to homogenize. Upon completing addition of phase D, homogenize for 15 min at 80° C. then begin cooling the mixture. At 60° C. switch to paddle mixing, using moderate agitation. Phase E is added and mixed until a homogenous mixture obtained. At 50° C. phase F is added. The mixture is cooled until it reaches room temperature.

Press Powder Eye Shadow (Purple)

| INCI Name | Trade Name | Supplier | Parts |
|---|---|---|---|
| Mica | Sericite PHN | Presperse | 75.60 |
| Zinc Stearate | Zinc Stearate | Witco | 5.00 |
| Colorant | Encapsulated TiO$_2$ | Ciba Specialty Chemicals | 6.00 |
| Colorant | Encapsulated Red Pigment | Ciba Specialty Chemicals | 2.00 |
| Colorant | Encapsulated Blue Pigment | Ciba Specialty Chemicals | 0.60 |
| Methylparaben | Nipagin M | Clariant | 0.20 |
| Propylparaben | Nipasol M | Clariant | 0.10 |
| Calcium Aluminum Borosilicate | Luxsil | Presperse | 5.00 |
| PEG-4 Diheptanoate | Liponate 2-DH | Lipo | 5.50 |
|   |   | Total | 100.00 |

Procedure:

Combine ingredients and mix well. Heat to 100° C. and press at 2000 psi.

What is claimed is:

1. Microparticles comprising a matrix polymer containing an effective coloring amount of at least 1 colorant and secondary particles distributed throughout the matrix polymer, wherein said colorant is entrapped in the matrix polymer, which matrix polymer is impermeable to the colorant and has been formed from a blend of monomers comprising a first monomer which is an ethylenically unsaturated ionic monomer and a second monomer which is an ethylenically unsaturated hydrophobic monomer selected from styrene, methyl methacrylate, tertiary butyl methacrylate, phenyl methacrylate, cyclohexyl methacrylate and isobornyl methacrylate which is capable of forming a homopolymer of glass transition temperature in excess of 50° C., and wherein the secondary particles comprise a core of a hydrophobic polymer that has been formed from an ethylenically unsaturated hydrophobic monomer selected from styrene, methyl methacrylate, tertiary butyl methacrylate, phenyl methacrylate, cyclohexyl methacrylate and isobornyl methacrylate which is capable of forming a homopolymer having a glass transition temperature in excess of 50° C. and optionally other monomers, which hydrophobic polymer is different from that of the matrix polymer, and which core is surrounded by a shell comprising the matrix polymer of the microparticle.

2. Microparticles according to claim 1, which have a particle size of between 1 and 60 microns.

3. Microparticles according to claim 1 in which the colorant is at least one pigment, dye or lake.

4. Microparticles according to claim 1, in which the colorant is an organic or inorganic pigment, a lake, or a mixture thereof.

5. Microparticles according to claim 1, which comprise further active ingredients.

6. A solid or liquid personal care or cosmetic composition that comprises a cosmetically tolerable carrier or adjuvant and an effective coloring amount of a blend of at least 2 colorants, wherein said colorants are entrapped in one or more microparticulate matrix polymers which are impermeable to the colorant and have been formed from a blend of monomers comprising a first monomer which is an ethylenically unsaturated ionic monomer and a second monomer which is an ethylenically unsaturated hydrophobic monomer selected from styrene, methyl methacrylate, tertiary butyl methacrylate, phenyl methacrylate, cyclohexyl methacrylate and isobornyl methacrylate which is capable of forming a homopolymer of glass transition temperature in excess of 50° C., wherein secondary particles are distributed throughout the one or more microparticulate matrix polymers, which secondary particles comprise a core of a hydrophobic polymer that has been formed from an ethylenically unsaturated hydrophobic monomer selected from styrene, methyl methacrylate, tertiary butyl methacrylate, phenyl methacrylate, cyclohexyl methacrylate and isobornyl methacrylate which is capable of forming a homopolymer having a glass transition temperature in excess of 50° C. and optionally other monomers, which hydrophobic polymer is different from that of the matrix polymer, and which core is surrounded by a shell comprising the one or more matrix polymer.

7. A composition according to claim 6, wherein the entrapped colorants in the composition are selected from at least two colors that are distinct from each other.

8. A composition according to claim 6, wherein the entrapped colorants in the composition are selected from at least two primary of the primary colors red, yellow and blue.

9. A composition according to claim 6, wherein the entrapped colorants in the composition are provided in at least 2 separate matrix polymer materials.

10. A composition according to claim 6, wherein at least 2 entrapped colorants are present within a single matrix polymer material.

11. A composition according to claim 6, which comprises from 0.1 to 70% by weight the blend of entrapped colorants based on the total weight of the composition.

12. A composition according to claim 6, which is formulated as a water-in-oil or oil-in-water emulsion, as a vesicular dispersion of an ionic or non-ionic amphiphilic lipid, as a gel, or a solid stick.

13. A composition according to claim 6, which is in the form of a skin-care preparation, a cosmetic personal care preparation or a light-protective preparation.

14. A composition according to claim 6 which is incorporated into a facial make-up in the form of lipsticks, eye shadow, liquid make-up, day creams or powders, facial lotions, creams or powders.

15. A composition according to claim 6, which comprises at least one further constituent selected from the group consisting of sequestering agents, non-encapsulated colorants, perfumes, thickening or solidifying agents, emollients, UV absorbers, skin-protective agents, antioxidants and preservatives.

* * * * *